United States Patent [19]

Brown, Jr. et al.

[11] 4,410,508

[45] Oct. 18, 1983

[54] NOVEL AQUEOUS FOAM FORMULATION AND METHOD

[75] Inventors: Harry A. Brown, Jr., Fallston; Robert F. Durgin, Abingdon, both of Md.

[73] Assignee: The United States of America as represented by the Secretary of the Army, Washington, D.C.

[21] Appl. No.: 275,540

[22] Filed: Jun. 19, 1981

Related U.S. Application Data

[62] Division of Ser. No. 69,034, Aug. 23, 1979, abandoned.

[51] Int. Cl.[3] .................... A61K 31/78; A01N 43/00; B01J 13/00

[52] U.S. Cl. .................................... 424/81; 252/307; 424/244

[58] Field of Search .................. 252/307; 424/244, 81

[56] References Cited

U.S. PATENT DOCUMENTS

| | | | |
|---|---|---|---|
| 1,970,578 | 8/1934 | Schoeller et al. | 252/DIG. 1 |
| 2,971,458 | 2/1961 | Kumins et al. | 252/307 X |
| 3,210,372 | 10/1965 | Werner et al. | 424/244 X |
| 3,713,404 | 1/1973 | Lavo et al. | 252/307 X |
| 3,814,808 | 6/1974 | Schwendeman et al. | 252/307 X |
| 4,203,974 | 5/1980 | Brown, Jr. et al. | 424/166 |

OTHER PUBLICATIONS

Chem. Abstracts, 84:;13183w (1976).

Chem. Abstracts, 84:70014r (1976).

*Primary Examiner*—Richard D. Lovering

*Attorney, Agent, or Firm*—Robert P. Gibson; Anthony T. Lane; A. Victor Erkkila

[57] ABSTRACT

A stable high expansion foam formulation for use as a single composite solution containing dibenz-(b,f)-1,4-oxazepine and stabilizers selected from the group consisting of glycerine, carboxyl vinyl polymers, and mixtures thereof. A method of using novel high expansion foam for visual obscuration and area denial is also disclosed.

4 Claims, No Drawings

NOVEL AQUEOUS FOAM FORMULATION AND METHOD

DEDICATORY CLAUSE

The invention described herein may be manufactured, licensed, and used by or for the Government for governmental purposes without the payment to us of any royalty thereon.

This application is a continuation of application Ser. No. 69,034, filed Aug. 23, 1979 (now abandoned).

BACKGROUND OF THE INVENTION

The invention relates to a new, stable high-expansion aqueous foam formulation containing dibenz-(b,f)-1,4-oxazepine and stabilizers selected from glycerine, carboxyl vinyl polymers, and mixtures thereof.

The invention also relates to a method of obtaining visual obscuration and area denial in military operations through use of a novel, stable, high-expansion aqueous foam formulation containing dibenz-(b,f)-1,4-oxazepine in sufficient quantities to provide area denial for extended periods of time.

The invention further relates to an aqueous foam formulation which will remain stable even when stored for extended periods of time under severe environmental stress conditions.

The invention still further relates to an aqueous foam formulation containing dibenz-(b,f)-1,4-oxazepine as a deterrent which will adhere to the surface of objects or persons entering or moving about in a foam generated from the formulation.

The invention also relates to a foam formulation which can be used as a single composite solution or as two separate solutions to be mixed immediately prior to foam generation in conventional fire fighting foam generators.

Prior foam formulations have generally been adequate for achieving visual obscuration for short periods of time. Previous studies on foam formulations have used high expansion foams as carriers for selected deterrent chemicals such as military tear gas (CS), but these foams have exhibited inadequate foam stability in conjunction with a high liquid drainage rate. Only short-term effectiveness in visual obscuration and area denial have been achieved. An aqueous foam formulation containing ammonia developed by applicants and described in copending U.S. Pat. application, Ser. No. 886,961, filed Mar. 15, 1978, now U.S. Pat. No. 4,203,974 has succeeded in providing extended term stability of foam for both visual obscuration and area denial, but this requires the use of a relatively large amount of ammonia to achieve a deterrent effect which is less effective than the relatively small amounts of dibenz-(b,f)-1,4-oxazepine (CR) deterrent compound used in the present invention.

SUMMARY OF THE INVENTION

A novel, stable aqueous foam formulation for use as a single composite solution comprising a conventional high expansion foam concentrate, dibenz-(b,f)-1,4-oxazepine and stabilizer and thickening materials selected from glycerin, carboxyl vinyl polymers and mixtures thereof.

It is the principal object of this invention to provide a high-expansion aqueous foam formulation containing dibenz-(b,f)-1,4-oxazepine (CR) as a deterrent compound for area denial.

Another object of this invention is to provide an aqueous foam formulation containing CR that is stable and effective for visual obscuration and area denial over an extended period of time.

A further object of this invention is to provide a method for visual obscuration and area denial through the use of a high expansion foam formulation which includes CR in sufficient quantities to serve as a deterrent.

A still further object of this invention is to provide an aqueous foam formulation containing the deterrent compound CR which will adhere to objects and persons with the generated foam.

These and other objects will become apparent from the following detailed description of the invention.

DESCRIPTION OF THE INVENTION

The aqueous foam formulation of this invention comprises a commercially available high expansion foam liquid concentrate for use in visual obscuration and dibenz-(b,f)-1,4-oxazepine as a deterrent compound for area denial. The foam formulation also includes conventional thickening and stabilizing materials for foam stability during storage and for ease of dissemination by conventional foam generation apparatus, such as that used for fire fighting purposes. In a preferred foam, the incorporation of the stabilizers glycerin and a carboxyl vinyl polymer, available commercially as C-941 TM from B. F. Goodrich Chemical Co., Cleveland, Ohio, produces a "sticky" foam which adheres to the surfaces of objects or persons entering or moving about in the foam. The desired visual obscuration effect of the foam is thus enhanced and the foam tends to clog or block the air ports of non self-contained breathing devices, such as gas masks, which could otherwise be used to defeat the deterrent effect of the dibenz-(b,f)-1,4-oxazepine (CR).

The aqueous foam formulation of this invention can be prepared using any one of a number of high expansion foam liquid concentrates which are conventionally available for use in producing known fire fighting foams. In particular, the high expansion foam concentrate principally consists of a "foaming agent," i.e., surfactant such as sodium lauryl sulfate and/or polyoxyethylated lauryl alcohol and derivatives thereof as principal active ingredients which are spumable in aqueous dispersion and adapted in such form to provide the continuous phase which constitutes the walls of the bubbles in the high expansion foam derived therefrom. In addition to a spumed by pneumatic or mechanical means into a three-dimensional foam structure, the foam agent in aqueous dispersion must be chemically unreactive with the dibenz-(b,f)-1,4-oxazepine added to the concentrate in the instant foam formulation.

High expansion foams, as used in the instant invention, are conventionally known in the art, as shown in the U.S. Pat. No. 3,713,404, to Lavo et al, dated Jan. 30, 1973, for plant industry application of high expansion foams containing chemical and biological agents for use in treating plant life. Reference is to be had to the above United States patent to Lavo et al which discloses, for example at Col. 6, lines 32–66, high expansion foam concentrates containing sodium lauryl sulfate and/or lauryl sulfates and sulfonates which can be used in the formulation of this invention. The referenced patent to Lavo et al also discloses representative stabilizers, such as the glycerol, at Col. 7, lines 30-37, which can be used to improve stability of the instant foam formulation, as well as other additives which can be used to improve foaming and fluidity.

The preferred aqueous foamable formulation of this invention comprises a high expansion foam liquid concentrate capable of generating a high-expansion foam and is prepared from the principal active foam ingredient selected from the surfactant sodium lauryl sulfate and/or polyoxyethylated lauryl alcohol includes derivatives thereof in mixtures with distilled water, glycerol and a high molecular weight carboxyl vinyl polymer (available from B. F. Goodrich Chemical Co., Cleveland, Ohio, under the trade name C-941) as thickening and stabilizing agents and the deterrent compound dibenz-(b,f)-1,4-oxazepine (CR). The mixture is stored as a single composite solution in a glass or stainless steel, closed container up until the time the foam is generated. Alternatively, two separate solutions can be prepared, such as (1)dibenz-(b,f)-1,4-oxazepine dissolved in the high expansion foam concentrate and (2) the carboxyl vinyl polymer dissolved in water followed by addition of glycerol and stored in separate containers for mixing immediately prior to foam generation.

The novel foam formulations of this invention can be best understood by reference to the following specific examples, which are meant to be merely illustrative and not a limitation upon the scope of this invention.

EXAMPLES. Various combinations of potential thickening and stabilizing materials were used during the development of dibenz-(b,f)-1,4-oxazepine containing foam formulations. The preferred foam formulation for both stability and extended visual and deterrent application had the following formulation:

EXAMPLE 1

| Component | Weight percent |
|---|---|
| Distilled water | 83.625 |
| Glycerol | 10. |
| HEF concentrate* | 6. |
| Carbopol 941** | 0.275 |
| Dibenz-(b,f)-1,4-oxazepine | 0.1 |

wherein *HEF concentrate is a foam concentrate containing sodium lauryl sulfate and polyoxyethylated lauryl alcohol surfactant as the principal active ingredient liquid foam concentrate, available for example from National Foam Systems, Inc., Lionsville, Pa., and **C-941 is a conventional high molecular weight carboxyl vinyl polymer thickener which is characterized by constant viscosity at a pH range of 4-11 and which is available from B. F. Goodrich Chemical Co., Cleveland, Ohio.

The above components of the foam formulation were mixed as follows: Dibenz-(b,f)-1,4-oxazepine was dissolved in the HEF liquid concentrate. The Carbopol 941 carboxyl vinyl polymer was then dissolved in distilled water and after complete solution of the C-941, the glycerol was added. The two solutions were then mixed together using only the minimum stirring necessary to provide homogeneity without excessive foaming in the mixing vessel. The mixture is then stored in a glass or stainless steel, closed container up until the time the foam is generated in a conventional foam generator, such as that used in fire fighting. Alternatively, the two solutions could be mixed just prior to foam generation.

The foam produced had an extended-term stability when stored at ambient temperatures for periods of up to three months, with only a minor decrease in resulting foam stability upon generation. The incorporation of glycerol and the Carbopol 941 polymer stabilizer produced a foam with the added benefit of adherence to objects, e.g., eyeglasses or persons entering or moving about in the foam. Adherence enhances visual obscuration and tends to clog or block the air ports of non self-contained breathing devices, such as gas masks, which would possibly be employed to defeat the deterrent effects of the dibenz-(b,f)-1,4-oxazepine riot control agent.

Other examples of the aqueous foam formulations of this invention were prepared in the same manner as the example above, using varying amounts of dibenz-(b,f)-1,4-oxazepine, high expansion foam concentrate, and glycerol and carboxyl vinyl polymer stabilizing additives. In addition to the optimum formulation disclosed above, similar stability of foam, storage stability of the mixture and CR agent as well as superior obscuration and agent carrying capabilities were found with foam formulations having the following preferred ranges of components by weight percent;

dibenz-(b,f)-1,4-oxazepine up to 0.15%, C-941 of between 0.2 and 0.3 wt %; concentrate between 5.0 and 7.0 wt % and glycerol between 8.0 and 12.0 wt %.

Another high expansion foam liquid concentrate which produced a foam of good stability, though it did not remain stable for four hours as required for present military applications, is illustrated below. This alternate foam concentrate consisting essentially of the principal active ingredients triethanolamine lauryl sulfate and lauryl dimethyl amine oxide (lauramine oxido) in aqueous solution.

Example: Aqueous foam formulations were prepared using 5 wt % triethanolamine lauryl sulfate (MAPROFIX TLS 500™ from Onyx Chemicals) and 1% (wt) lauryl dimethyl amine oxide (AMMONYX LO ™ from Onyx Chemicals) were prepared alternatively with 10% (wt) glycerin and 84% water (Run 18); 10% ethylene glycol and 84% water (Run 38); and 10% ethylene glycol, 0.3 carboxyl vinyl polymer (Carbopol 941™) and 83.7% water (Run 39) with the results tabulated below:

| | RUN 18 | RUN 38 | RUN 39 |
|---|---|---|---|
| Pressure on supply | 15 psig | 15 psig | 35 |
| Vol. foam solution (ml) | 190 | 200 | 200 |
| Vol. foam produced (7) | 114.0 | 137.4 | 0 |
| Expansion Ratio | 600 | 687 | — |
| Viscosity (23° C.) CS | 1.4 | 1.4 | 1043.7 |
| pH | 6 | 6 | 6 |
| Vol. foam remaining: | | | |
| after 1 hr. | 83.2 | 64.6 | — |
| after 2 hr. | 59.2 | 35.4 | — |
| after 3 hr. | 31.4 | 0.4 | — |
| after 4 hr. | 0.4 | 0 | — |
| Liquid drainage (%): | | | |
| after 1 hr. | *87.5 (**68.4) | *88.6 (**62.0) | — |
| after 2 hr. | *97.0 (75.8) | *98.6 (**69.0) | — |
| after 3 hr. | *98.3 (76.8) | *100.0 (**70.0) | — |
| after 4 hr. | *100.0 (65.0) | — | — |

*% of total volume collected.
**% of original volume before foaming.

Thus other substituted lauryl sulfates can provide a foam of relatively good stability, though these foam concentrates do not give a foam of the stability desired for a military foam achieved through use of the preferred foam concentration formulation.

A preferred high expansion foam concentrate, shown in Example 1, has sodium lauryl sulfate and polyoxyethylated lauryl alcohol as the principal active ingredient, i.e., surfactants, in water with cellosolve, capryl amide and ethanol as thickening and stabilizing materials similar to that commercially available under the tradename HI-EX, foam concentrate from National Foam Systems, Incorporated.

Though glycerin and the carboxyl vinyl polymer shown in Example 1 are the preferred thickener and stabilizer, there are a number of other conventional stabilizers and thickeners which could be used to give stable foams. Thus, hydroxypropyl cellulose (Klucel E TM and M TM from Hercules, Inc.); ethylene glycol; propolyene glycol; the alpha helix-shaped protein colloids having molecular weights of 40,000 (Technical Protein Colloid 1-V TM); mol. wt. 60,000 (Technical Protein Colloid 4-V TM); mol. wt. 80,000 (Technical Protein Colloid 5-V TM) and a long football-shaped protein, mol. wt. 80,000 (Technical Protein Colloid Fluid 2260 TM) all available from Swift Chemical Company's Technical Colloid Division; methylcellulose (Methocel 3475 TM by Dow Chemical Company); poly (ethylene oxide) resin of molecular weight 250,000–350,000 (Polyox WSR-35 TM from Union Carbide Corporation); and high molecular weight carboxyl vinyl polymers which have relatively constant viscosities over a range of pH from 4 to 11 (Carbopol 934, 960 and 941 TM from B. F. Goodrich Chemical Company).

The dibenz-(b,f)-1,4-oxazepine (CR) used in the foam formulation of this invention is a known riot control agent which was developed and used by the British Government. It has been adopted by the United States Army as a deterrent agent and has been also made available to civilian police agencies for potential civil riot control applications. The preparation of dibenz(b,f)-1,4-oxazepine ($C_{13}H_9NO$) is known in the art, as shown for example in the article, *Syntheses of Heterocyclic Compounds Cyclisation of O-Nitrophenyl Oxygen Ethers*, Journal of The Chemical Society, Part II, pp. 2367–2370, published by the Chemical Society, London, England, 1962. Prior art use of dibenz-(b,f)-1,4-oxazepine (CR) as a riot control agent in water "cannon" and comparing its effects with the tear gas (CS) is shown in the publication "Effects on Man of Drenching with Dilute Solutions of O-Chlorobenzylidene Malononitrile (CS) and Dibenz(b,f)-1:4-oxazepine (CR)", Medicine, Science, and the Law 16 (3), pp. 159–170 (1976).

The foam formulation of this invention can be generated in various types of apparatus conventionally used for foam generation, such as that used to generate aqueous foam for fire fighting purposes. The aqueous foam may be generated, for example, by spraying the foam formulation evenly over a mesh screen through which a gas, e.g., air, is passed at a controlled rate. Foam bubbles produced at the screen surface would be ejected by the force of the gas flow. Desired foam characteristics can be obtained by selective variation of liquid flow rate, nozzle size and spray pattern, screen mesh size and gas flow rate. A self-contained generator dispenser apparatus, such as the vehicle mounted XM 35El used by the military for generating riot control foams, is a suitable apparatus. The apparatus used to generate the novel foam formulation of this invention is not critical, however, and does not constitute a part of the invention.

The novel foam formulation of this invention has succeeded in providing a stable foam for visual obscuration and area denial through incorporation of the deterrent riot control compound dibenz-(b,f)-1,4-oxazepine. In particular, the foam formulation has achieved the goals of being effective at temperatures within the range of 0° to 110° F. (−17.7° to 43.3° C.); having a storage stability of more than 1 year at ambient conditions, an expansion ratio, i.e., volume of foam produced over volume liquid concentrate used of over 200 and a foam stability of over one hour and preferably four hours (foam stays at 80 percent of original generated foam height) without excessive drainage.

The specific amounts of the foamer concentrate, stabilizers and CR deterrent agent used in the foams can be varied within the skill of one in the art to achieve optimum foam stability and deterrent effects. Though the specific concentrations used in the foam have not been found to be critical for foam formulation, optimum foam stability characteristics have been found with foams having constituents within specific practically defined limits. In particular, it has been found that the foam formulation should have a "foamer" e.g., a sodium alkyl sulfonate and polyoxyethylated lauryl alcohol or derivatives thereof providing a surfactant concentrate which has a practical lower limit of 1 percent and an upper limit of approximately 12 percent, since greater concentrations tend to produce more inefficient, thicker foams. A 5–7 percent HEF concentrate weight percent of the final foam is preferred. The concentration of dibenz-(b,f)-1,4-oxazepine (CR) deterrent compound needed is very low, with a practical upper limit being of the order of 0.15% wt since this corresponds to its solubility limit in the total foam formulation, with larger amounts salting out of solution. The thickening and stabilizing additives glycerol and carboxyl vinyl polymers have practical upper limits of 12% and 0.3%, respectively, since higher concentrations will result in an undesirable thick solution at ambient temperatures. The thickness of the solution will vary with temperatures, however, and larger amounts could be used at higher temperatures.

The essential features of this invention are that the foam formulations yield a high expansion foam which will remain stable for a period of up to 4 hours and which will provide sustained visual obscurates while containing the deterrent compound CR. Though the term high expansion foam, as used in the art, is susceptible to a broader construction, the use of foams for military and riot control purposes indicates the use of foams having an expansion ratio of at least 200 up to a maximum of 1000, with a practical preferred limit of from 200 to 700.

The novel foam formulation of this invention can obviously be modified by including additional deterrent agents, either as an additional deterrent or as a replacement for the CR. Morover, the CR can also be deleted if only a foam for visual obscuration is desired.

The deterrent agent foam formulation of this invention provides a single composite solution which is readily disseminated by conventional means and which has superior stability for extended periods of time. The foam formulation thus allows visual obscuration and effective area denial through use of a stable foam which will adhere to persons in the dissemination area.

Applicants having disclosed their invention, obvious modification will become apparent to those skilled in the related chemical fields. Applicants therefore wish to be limited only by the scope of the appended claims.

We claim:

1. An aqueous composition suitable for providing a high expansion foam having an expansion ratio of at least 200 and a stability of about 4 hours or more, said aqueous composition consisting essentially of 1% to 12% mixture of sodium lauryl sulfate and polyoxyethylated lauryl alcohol 8% to 12% glycerol 0.2% to 0.3% carboxyl vinyl polymer up to 0.15% dibenz-(b,f)-1,4-oxazepine and water, percentages being by weight based on the aqueous composition.

2. A composition according to claim 1, containing 5.0% to 7% of the mixture of sodium lauryl sulfate and polyoxyethylated lauryl alcohol.

3. A method of obtaining visual obscuration and area denial in military and riot control operations, which comprises disseminating a stable, high expansion foam consisting essentially of an aqueous composition consisting essentially of 1% to 12% mixture of sodium lauryl sulfate and polyoxyethylated lauryl alcohol 8% to 12% glycerol 0.2% to 0.3% carboxyl vinyl polymer up to 0.15% dibenz-(b,f)-1,4-oxazepine and water, percentages being by weight based on the aqueous composition, as a deterrent to persons exposed to said foam.

4. A method according to claim 3, wherein the aqueous composition contains between 5.0% and 7% of the mixture of sodium lauryl sulfate and polyoxyethylated lauryl alcohol.

* * * * *